United States Patent
Ulmann et al.

(10) Patent No.: US 12,288,323 B2
(45) Date of Patent: Apr. 29, 2025

(54) MAPPING IMAGE SIGNATURES OF CANCER CELLS TO GENETIC SIGNATURES

(71) Applicant: KONINKLIJKE PHILIPS N.V., Eindhoven (NL)

(72) Inventors: Shrutin Ulmann, Bangalore (IN); Prasad Raghotham Venkat, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 619 days.

(21) Appl. No.: 17/285,745

(22) PCT Filed: Oct. 15, 2019

(86) PCT No.: PCT/EP2019/077915
§ 371 (c)(1),
(2) Date: Apr. 15, 2021

(87) PCT Pub. No.: WO2020/078974
PCT Pub. Date: Apr. 23, 2020

(65) Prior Publication Data
US 2022/0004737 A1 Jan. 6, 2022

Related U.S. Application Data

(60) Provisional application No. 62/746,612, filed on Oct. 17, 2018.

(51) Int. Cl.
*G06T 7/00* (2017.01)
*G06V 10/764* (2022.01)
(Continued)

(52) U.S. Cl.
CPC .......... *G06T 7/0012* (2013.01); *G06T 7/0014* (2013.01); *G06V 10/764* (2022.01);
(Continued)

(58) Field of Classification Search
CPC ................. G06T 7/0012; G06T 7/0014; G06T 2207/20081; G06T 7/00; G06T 1/00;
(Continued)

(56) References Cited

U.S. PATENT DOCUMENTS 6,007,996 A * 12/1999 McNamara .......... G01N 33/582
 435/7.1
8,306,185 B2 * 11/2012 Bal ........................ G16H 20/40
 378/65

(Continued)

FOREIGN PATENT DOCUMENTS

CA 2631564 A1 * 6/2006 ........... A61B 5/0059
CA 2791624 A1 * 9/2011 ........... A61B 5/0059
(Continued)

OTHER PUBLICATIONS

Henry et al., "Surface-Enhanced Raman Spectroscopy Biosensing: In Vivo Diagnostics and Multimodal Imaging" (pp. 6638-6647) (Year: 2016).*

(Continued)

*Primary Examiner* — Manav Seth

(57) ABSTRACT

A method and system for treating a patient is described. The method includes: (i) receiving a sample from a patient, the sample including one or more cancer cells; (ii) obtaining, using an imaging device, one or more images of the cancer cells; (iii) processing, using an imaging processor, the one or more images to extract one or more image coefficients; (iv) mapping, using a trained classifier, the one or more image coefficients to a cancer cell type; (v) identifying, based on mapping the one or more image coefficients to a cancer cell type, one or more cancer cell types in the sample; (vi) identifying, based on the identified one or more cancer cell types in the sample, a course of treatment specific to the one (Continued)

or more cancer cell types; and (vii) treating the patient using the identified course of treatment.

16 Claims, 2 Drawing Sheets

(51) Int. Cl.
    *G06V 20/69*     (2022.01)
    *G16H 10/40*     (2018.01)
    *G16H 15/00*     (2018.01)
    *G16H 20/00*     (2018.01)
    *G16H 30/40*     (2018.01)
    *G16H 50/20*     (2018.01)

(52) U.S. Cl.
    CPC ........... *G06V 20/698* (2022.01); *G16H 10/40* (2018.01); *G16H 15/00* (2018.01); *G16H 20/00* (2018.01); *G16H 30/40* (2018.01); *G16H 50/20* (2018.01); *G06T 2207/20081* (2013.01); *G06T 2207/30024* (2013.01)

(58) Field of Classification Search
    CPC ...... G06T 2210/41; G06T 2207/30024; G06V 10/764; G06V 20/698; G06V 10/10; G06V 10/74; G06V 2201/031; G06V 2201/03; G16H 10/40; G16H 15/00; G16H 20/00; G16H 30/40; G16H 50/20; G16H 30/20; G16H 50/70
    See application file for complete search history.

(56) References Cited

U.S. PATENT DOCUMENTS

| | | | |
|---|---|---|---|
| 8,597,899 B2 | 7/2013 | Gough | |
| 11,145,411 B2 * | 10/2021 | Treado | G16H 50/20 |
| 2003/0065156 A1 * | 4/2003 | Williams | C07K 14/47 |
| | | | 435/7.1 |
| 2006/0253261 A1 * | 11/2006 | Maier | G01N 21/65 |
| | | | 702/19 |
| 2014/0377753 A1 | 12/2014 | Bamford | |
| 2021/0104028 A1 * | 4/2021 | Gomer | G01N 33/4833 |

FOREIGN PATENT DOCUMENTS

| | | | | |
|---|---|---|---|---|
| EP | 3721406 B1 * | 1/2024 | ........... | G06T 7/0012 |
| WO | WO-2009021178 A1 * | 2/2009 | ........... | A61B 5/0059 |
| WO | WO-2011106792 A2 * | 9/2011 | ........... | A61B 5/0059 |
| WO | WO-2014074569 A1 * | 5/2014 | ............. | G01N 21/65 |
| WO | 2016087589 A1 | 6/2016 | | |
| WO | 2016134211 A1 | 8/2016 | | |
| WO | 2017087415 A1 | 5/2017 | | |
| WO | WO-2018005355 A1 * | 1/2018 | ....... | G01N 33/57492 |
| WO | WO-2018086985 A1 * | 5/2018 | ......... | G06K 9/00147 |
| WO | WO-2019025533 A1 * | 2/2019 | ......... | G01N 15/1433 |
| WO | WO-2019110583 A1 * | 6/2019 | ......... | G06F 18/2431 |

OTHER PUBLICATIONS

Plas et al., "Image fusion of mass spectrometry and microscopy: a multimodality paradigm for molecular tissue mapping" (pp. 366-374) (Year: 2015).*
Lee et al., "Fabrication of SERS-fluorescence dual modal nanoprobes and application to multiplex cancer cell imaging" (pp. 124-129). (Year: 2012).*
Bellisola et al., "Infrared spectroscopy and microscopy in cancer research and diagnosis" (pp. 1-21) (Year: 2012).*
International Search Report Dec. 10, 2019.
Hanchuan Peng et al, "Automatic Image Analysis for Gene Expression Patters of Fly Embryos", Jul. 10, 2007, pp. 1-13.
Spagnolo M. Daniel et al, "Pointwise Mutual Information Quantifies Intratumor Heterogeneity in Tissue Sections Labeled With Multiple Fluorescent Biomarkers", Jouran of Pathology Informatics, Nov. 29, 2016.
Gurcan M. N. et al., "Histopathological Image Analysis: a Review", IEEE Reviews in Biomedical Engineering, IEEE, USA, vol. 2, Jan. 1, 2009, pp. 147-171.
Conference Paper et al, "Using Deep Learning To Enhance Cancer Diagnosis and Classification Using Deep Learning To Enhance Cancer Diagnosis and Classification", Jan. 1, 2013.

* cited by examiner

MAPPING IMAGE SIGNATURES OF CANCER CELLS TO GENETIC SIGNATURES

This application is the U.S. National Phase application under 35 U.S.C. § 371 of International Application No. PCT/EP2019/077915, filed on Oct. 15, 2019, which claims the benefit of U.S. Provisional Application Ser. No. 62/746,612, filed Oct. 17, 2018. These applications are hereby incorporated by reference herein.

FIELD OF THE DISCLOSURE

The present disclosure is directed generally to methods and systems for identifying the genetic signature of a cancer cell type using image processing.

BACKGROUND

Costs associated with cancer care have skyrocketed, and are rising year by year. According to research, the spending in a cancer-afflicted household is 35-44% more than in other households. The extremely high costs associated with cancer treatment, whether it is chemotherapy drugs, radiotherapy, or other treatment methods, further add to the stress and impact of a cancer diagnosis. Additionally, the incidence of cancer is rising in the 36-45 year old age group, which is in the middle of the prime career-building portion of an individual's lifetime. These factors demonstrate that cancer treatment is a serious issue facing both individuals and world economies.

Cancer costs trajectories plotted using data from various countries indicate that early diagnosis and optimal therapy (optimal in both time and type) can potentially bring down costs associated with cancer care. Additionally, involving local primary care hospitals in palliative care can improve treatment success and further lower treatment costs.

Correctly identifying a patient's cancer type, as early as possible, can significantly improve treatment outcome and lower treatment costs. There are many different methods for characterization of cancer cell type. Among the most prominent is genetic analysis, which identifies a genetic signature associated with a cancer cell type. However, genetic analysis can be expensive, particularly in developing regions of the world.

SUMMARY OF THE DISCLOSURE

There is a continued need for methods and systems that quickly and affordably identify the genetic signature of a cancer cell type.

The present disclosure is directed to inventive methods and systems for identifying the genetic signature of a cancer cell type using image processing. Various embodiments and implementations herein are directed to a method and system configured to map cancer cell imaging parameters to a genetic signature associated with those imaging parameters. Cancer cells from a patient are imaged and one or more image coefficients are extracted from the images using imaging processing. A trained classifier maps the extracted image coefficients to a genetic signature specific to a cancer cell type, and a course of treatment specific to the identified cancer cell type is identified. The patient is then treated using the identified course of treatment.

Generally, in one aspect, a method for treating a patient is provided. The method includes: (i) receiving a sample from a patient, the sample comprising one or more cancer cells; (ii) obtaining, using an imaging device, one or more images of the cancer cells; (iii) processing, using an imaging processor, the one or more images to extract one or more image coefficients; (iv) mapping, using a trained classifier, the one or more image coefficients to a cancer cell type; (v) identifying, based on mapping the one or more image coefficients to a cancer cell type, one or more cancer cell types in the sample; (vi) identifying, based on the identified one or more cancer cell types in the sample, a course of treatment specific to the one or more cancer cell types; and (vii) treating the patient using the identified course of treatment.

According to an embodiment, the cancer type is a cancer sub-type.

According to an embodiment, the step of mapping further comprises mapping the one or more image coefficients to a genetic signature.

According to an embodiment, the method further includes the step of reporting the identified course of treatment.

According to an embodiment, the method further includes the step of obtaining information of a second mode about the cancer cells, wherein processing the one or more images to extract one or more image coefficients comprises processing the obtained images and the obtained information of a second mode;

According to an embodiment, the method further includes the step of training the classifier to map image coefficients to a cancer cell type.

According to an embodiment, the sample is, for example, a biopsy or a body fluid.

According to an embodiment, the step of processing comprises fractal-based image processing, wavelet-based image processing, spectroscopic image processing, and/or pattern-matching image processing.

According to an aspect, a system configured to identify a course of treatment specific to an identified cancer cell type is provided. The system includes: (i) a sample from an individual, the sample comprising one or more cancer cells; (ii) a first imaging device configured to obtain one or more images of the cancer cells; (ii) a processor configured to process the one or more images to extract one or more image coefficients; (iii) a trained classifier configured to: map the one or more image coefficients to a cancer cell type; and identify, based on mapping the one or more image coefficients to a cancer cell type, one or more cancer cell types in the sample; wherein the processor is further configured to identify, based on the identified one or more cancer cell types in the sample, a course of treatment specific to the one or more cancer cell types.

According to an embodiment, the system includes a cancer cell type database comprising a plurality of cancer cell types each associated with one or more image coefficients, wherein the trained classifier utilizes the cancer cell type database to map the one or more image coefficients to the cancer cell type.

According to an embodiment, the system includes a treatment plan database comprising a plurality of treatment plans each associated with a cancer cell type, wherein the processor utilizes the treatment plan database to identify a course of treatment.

According to an embodiment, the system includes a user interface configured to provide a report of the identified course of treatment to a user.

According to an embodiment, the trained classifier is further configured to map the one or more image coefficients to a genetic signature.

According to an embodiment, the system includes a second imaging device of a mode different from the first imaging device, the second imaging device configured to obtain information about the cancer cells.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various embodiments of a system and method for improving the treatment of cancer by improving the speed and accuracy with which cancer cell types are identified. More generally, Applicant has recognized and appreciated that it would be beneficial to provide a system that uses image processing to identify cancer cell types. Using the system, a trained classifier maps image coefficients extracted from images of cancer cells to a genetic signature specific to a cancer cell type. The system identifies a course of treatment specific to the identified cancer cell type, and the patient is treated using the identified course of treatment. Early identification of the proper course of treatment using an affordable diagnosis system provides personalized care that improves quality of life and reduces the cost and duration of cancer treatment.

Figure 1:
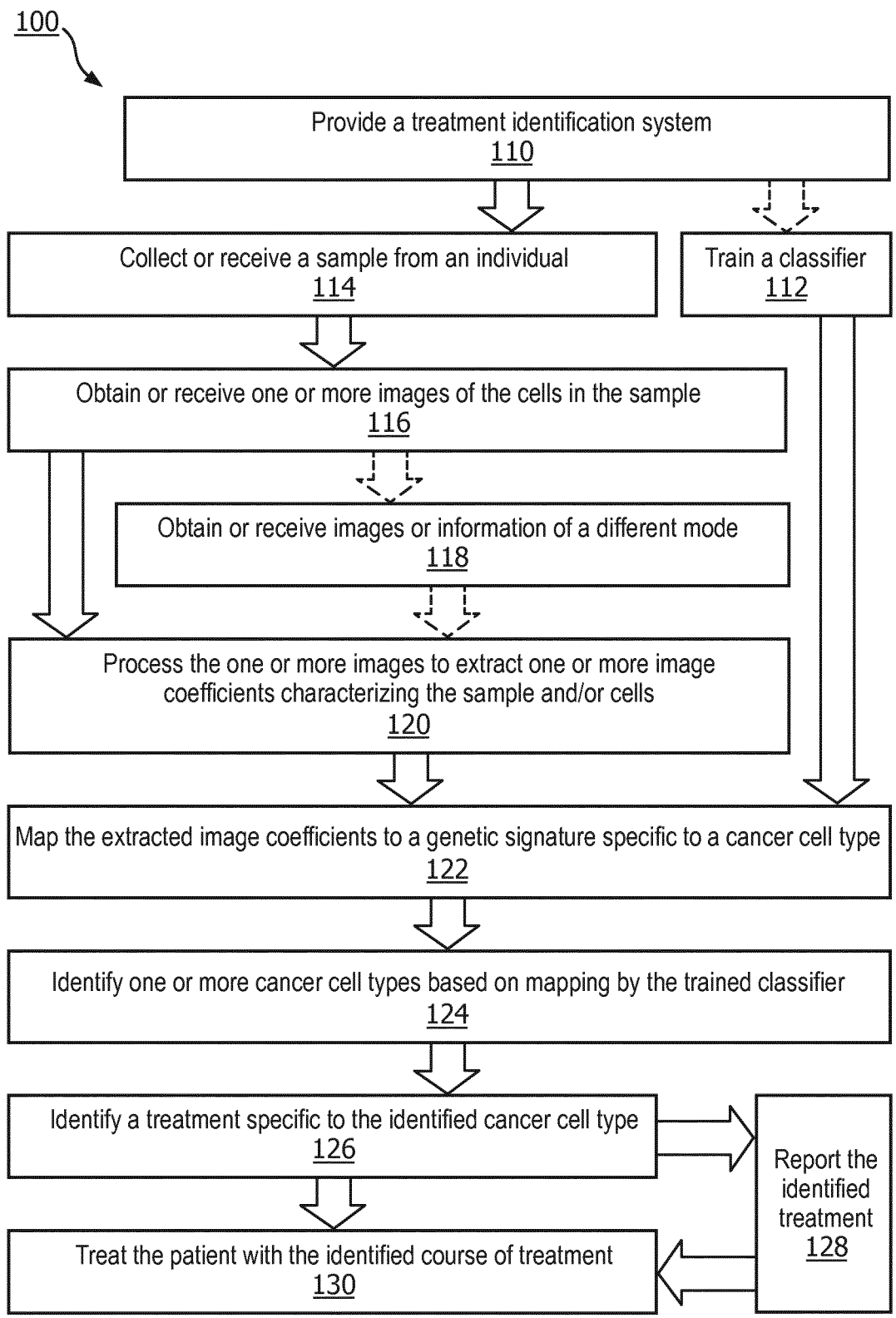
FIG. 1 is a flowchart of a method for treating a patient diagnosed with cancer, in accordance with an embodiment.

Referring to FIG. 1, in one embodiment, is a flowchart of a method 100 for treating a patient diagnosed with cancer by identifying a treatment specific to the patient's cancer cell type. The methods described in connection with the figures are provided as examples only, and shall be understood not to limit the scope of the disclosure. At step 110 of the method, a system configured to identify a cancer cell type, and to identify a course of treatment based on that identified cancer cell type, using image processing is provided, obtained, installed, or otherwise identified or activated. The treatment identification system can be any of the systems described or otherwise envisioned herein. According to an embodiment, the treatment identification system comprises one or more of an imaging device, an image processor, a trained classifier, a database of cancer cell types with correlated imaging coefficients and genetic signatures, a database of cancer treatments correlated with cancer cell types, and/or other elements or components.

The trained classifier of the treatment identification system can be any classifier capable of or configured for the image processing and/or image coefficient mapping described or otherwise envisioned herein. The classifier may be a neural network, a decision tree, a support vector machine, a linear classifier, random forest, and/or any other type of classifier or classification algorithm. The classifier is trained or otherwise designed or modified before installation, during installation, and/or after installation. Accordingly, at step 112 of the method, a classifier is trained. According to an embodiment, the classifier is trained with input collected by or provided to the system or classifier. The input may be any input, including information about a plurality of cancer cell types, one or more genetic signatures associated with each of a plurality of cancer cell types, and/or one or more image coefficients associated with each of a plurality of cancer cell types. For example, the classifier may be trained with input comprising an identified cancer cell type and the genetic signature and image coefficients associated with that identified cancer cell type. Accordingly, the classifier is trained to identify a cancer cell type and an associated genetic signature using one or more image coefficients.

The image coefficients associated with the identified cancer cell type may be any image coefficient, but are at least the image coefficients that will be utilized by the specific system in which the trained classifier is installed. For example, the image coefficient can be any quantifiable aspect of an image obtained from a cell, which can be reduced to a number. This quantifiable aspect, and the resulting number, is obtained using one or more imagine processing techniques such as fractals, wavelets, spectroscopy, and more.

According to an embodiment, once the trained classifier is built or designed, the classifier can be tested and validated to determine whether the model is functional and to optionally characterize one or more parameters of the model.

At step 114 of the method, a sample from an individual is provided. The sample may comprise cancer cells, be suspected to comprise cancer cells, or only randomly comprise cancer cells. For example, the sample may be any sample obtained from an individual, such as from a tumor, or from a tissue or location suspected to be or comprise a tumor. Tumor can be defined, for example, as a plurality of cancerous cells, and can be concentrated or diffuse. The tumor sample may be collected using any method or system for cell collection, such as through a biopsy or other tumor collection method. Since an embodiment of the method may only require a few cells, the sample can be collected and optionally concentrated from a body fluid or other diffuse tissue such as blood, lymph fluid, spinal fluid, and other tissues or fluids.

According to an embodiment, the sample is received locally by the system or by a point-of-care device or location. For example, the sample can be obtained and processed immediately by the treatment identification system, and/or after some sample processing to isolate or otherwise prepare the cells for imaging. Point-of-care may be a hospital, physician's office, out-patient facility, a long-term care facility, in the field, and/or any other location. According to another embodiment, the sample is obtained remotely and is received locally by a treatment identification system. For example, the sample can be obtained at a first location such as in the field or at a first office or location, and can be received at and processed by the treatment identification system which is located at a facility or at a second office or location.

At step 116 of the method, one or more images of cells in the sample are obtained using an imaging device. The imaging device is or comprises any device or system that can obtain images or similar information from the cells in the sample. According to an embodiment, the imaging device comprises an imager configured to obtain images of one or more cells in the sample. The imager can be an image sensor such as a CCD or CMOS sensor, among others. For example, the imager may be a standalone camera, or may be a camera integrated into another device. The imaging device or imager may comprise or otherwise be in communication with a light source configured to illuminate the sample. According to an embodiment, the imager is a spectrometer or other device configured to obtain and measure a spectral component of the sample or components of the sample.

According to another embodiment, the imaging device or imager is an audiometric signal or other audio signal that obtains information from the cells in the sample. For example, the sample can be exposed to sound waves which are used to obtain information about the cells. In one embodiment, the sound waves are converted into light by the cells and photodetectors are utilized to receive and/or process the received light into information used by the system in downstream steps of the method. Many other methods of obtaining imaging or similar information from a sample are possible.

At optional step 118 of the method, the system obtains or receives information of a different mode from the sample. For example, if the system obtains or receives images from a CCD or CMOS sensor of an imager in step 116, the system also obtains or receives information in step 118 of a different mode from the sample, such as spectroscopic information and/or audiometric information. Many other methods of obtaining imaging or similar information from a sample are possible. Accordingly, the system will have information about the sample from at least two different imaging or analysis modes, and may optionally have information from three or more different modes.

At step 120 of the method, the treatment identification system processes the one or more images using an image processor and/or image processing algorithm in order to extract one or more image coefficients. An image coefficient may be any image coefficient that can be utilized by the treatment identification system and the trained classifier to identify the cancer cell type. For example, the image coefficient can be any quantifiable aspect of an image obtained from a cell, which can be reduced to a number. This quantifiable aspect, and the resulting number, is obtained using one or more imagine processing techniques.

According to an embodiment, the image processor and/or image processing algorithm can be any processor or algorithm capable of and/or configured to extract an image coefficient from the one or more images, where the images can be visual images, audiometrics from a photodetector, spectroscopy, and/or any other utilized imaging mode. Accordingly, the image processing algorithm can be a fractal-based image processing technique configured to process an image. The image processing algorithm can be a wavelet-based image processing technique configured to process an image. The image processing algorithm can be a spectroscopic image processing technique configured to process an image. The image processing algorithm can be a pattern-matching image processing technique configured to process an image. Many other image processing techniques are possible. Among other aspects, these image processing technique are configured to identify and quantify, as image coefficients, image features such as texture, roughness, smoothness, solidity, area, edges, heterogeneity, chemical composition, and/or other parameters of cells in the sample. The image processing technique are further configured to identify and quantify, as image coefficients, image features that are recognizable as cellular components or elements such as the contents of the cell, the nucleus, ribosomes, exosomes, vacuoles, and/or any other sub-cellular organelles or structures.

For all these reasons, according to an embodiment, cancer cells will have image coefficients which are different from the image coefficients associated with non-cancer cells. For example, cancer cells replicate quickly and these cells can be differentiated from the normal cells by their rapid multiplication. Cancer cells can also be different from non-cancer cells in their texture and the intracellular organelles of the nuclei, ribosomes, and exosomes, among many other structures, organelles, and features. According to an embodiment, the image coefficients vary based on the type, stage, and aggressiveness of the cancer cell type, among other factors.

Accordingly, during and following step 120 of the method, the treatment identification system comprises one or more image coefficients describing one or more parameters of the cancer cells in the sample, all extracted from the obtained imaging information. The one or more extracted image coefficients may be stored in short-term and/or long-term storage, and/or may be communicated or otherwise transmitted to another location for storage or processing.

At step 122 of the method, the trained classifier maps the one or more extracted image coefficients to a genetic signature specific to a cancer cell type. The trained classifier of the treatment identification system can be any classifier capable of or configured for the image processing and/or image coefficient mapping described or otherwise envisioned herein. The classifier may be a neural network, a decision tree, a support vector machine, a linear classifier, and/or any other type of classifier or classification algorithm. The classifier may be trained with, for example, input comprising an identified cancer cell type and the genetic signature and image coefficients associated with that identified cancer cell type. Accordingly, the classifier is trained to identify a cancer cell type and an associated genetic signature using one or more image coefficients.

According to an embodiment, the classifier may consult a database of known image coefficients associated with known cancer cell types and known genetic signatures. For example, an image coefficient such as a specific vacuole density, size, or count, or a range thereof, may be associated with breast cancer, prostate cancer, or any other type of cancer, and/or may be associated with a sub-type of breast cancer, prostate cancer, or any other type of cancer. Accordingly, when a cell is imaged and the vacuole density, size, or count falls within the specific count or the range, the classifier identifies the cell as being a specific type or sub-type of cancer cell. According to an embodiment, the image coefficient such as a specific vacuole density, size, or count, or a range thereof may therefore be associated with the genetic signature which is associated with that identified type or sub-type of cancer cell.

According to an embodiment, therefore, the one or more extracted image coefficients are provided to the trained classifier as input. The trained classifier analyzes or otherwise processes the provided image coefficients, including consulting a database for cancer cell types and/or genetic signatures associated with one or more of the provided image coefficients, and maps the provided image coefficients to a cancer cell type or sub-type. An identification of a cancer cell type or sub-type may be an output. The trained classifier may be designed or configured to provide an identification of multiple identified cancer cell types or sub-types as output. According to an embodiment, the trained classifier may be designed or configured to provide two or more options for possible cancer cell types or sub-types if a more definitive identification is not possible. Thus, the classifier may comprise a threshold or other mechanism to assist the classifier in determining whether there is an identification of just one cancer cell type or sub-type, multiple cancer cell types or sub-types, and/or no possible identification. According to an embodiment, the trained classifier may be trained or otherwise designed or programmed to weight provided image coefficients or the associations retrieved from a database in order to provide an identification of one possible cancer cell type or sub-type. For example, the trained classifier may be trained or otherwise designed or programmed to weight certain image coefficients or parameters more heavily than other coefficients or parameters. Image coefficients or parameters such as size, vacuole density, roughness, and/or other coefficients or parameters may be more determinative of cancer cell type or sub-type and thus will be more heavily weighted.

At step 124 of the method, the treatment identification system identifies one or more cancer cell types or sub-types in the sample based on the trained classifier's identification and/or mapping. In step 122, the trained classifier analyzes or otherwise processes the provided image coefficients, including consulting a database for cancer cell types and/or genetic signatures associated with one or more of the provided image coefficients, and maps the provided image coefficients to a cancer cell type or sub-type. In step 124, the trained classifier and/or the treatment identification system provides an identification of the cancer cell type or sub-type as an output. The identification may be only an internal identification provided within the treatment identification system, and/or the identification may be an externally-provided report or other communication or identification of the cancer cell type(s) or sub-type(s).

In step 126 of the method, the treatment identification system identifies a course of treatment specific to the identified one or more cancer cell types in the sample. The treatment identification system can leverage existing or generated databases correlating a genetic signature and/or identified cancer cell type or sub-type with a course of treatment. A genetic signature identified by the treatment identification system may be associated in a database with a chemosensitivity, radiosensitivity, or other plan, recommendation, study, research, and/or treatment. Knowing the cancer cell type or sub-type and an associated recommended course of treatment provides a personalized, optimum treatment therapy for the patient.

According to an embodiment, the treatment identification system comprises a database of treatment plans, treatment recommendations, research studies, protocols, and/or other therapies which are each associated with one or more cancer cell types or sub-types. For example, a specific cancer sub-type may be associated with a specific 4-month protocol of a specific multi-factor chemotherapy regimen. According to another example, a specific cancer mixture may be associated with a specific research study which is enrolling participants for treatment.

According to another embodiment, the treatment identification system is in communication with a database of treatment plans, treatment recommendations, research studies, protocols, and/or other therapies which are each associated with one or more cancer cell types or sub-types. For example, the treatment identification system may request or be granted access to a public or paid database of treatment plans and therapies associated with cancer types. Thus, the treatment identification system comprises a communication component configured to query or otherwise communicate with the public or paid remote database for information. For example, once a specific cancer cell type or sub-type is identified by the treatment identification system, the system can query the database via a wired and/or wireless network to retrieve one or more therapies or treatments associated with and/or recommended for treatment of that specific identified cancer cell type or sub-type. This provides an optimized therapy trajectory to the patient, selected for the best possible outcome and at a minimal cost.

At step 128 of the method, the treatment identification system provides a report of the therapy or treatment obtained or identified in step 126 of the method. This information may be reported via a user interface such as a computer, screen, paper report, electronic report, text message, print-out, or any of a variety of other reporting methods. The information may be provided to a medical professional, a technician, a patient, and/or any other individual.

At step 130 of the method, the patient is treated with the reported therapy or treatment plan. Typically, a physician or other healthcare professional will receive a report at step 128 of the method, and will implement the one or more therapies or treatments associated with and/or recommended for treatment of the specific cancer cell type or sub-type identified in the sample obtained from the patient. The physician or healthcare professional may modify or adapt the recommended or identified treatment plan based on one or more additional factors.

According to an embodiment, the treatment identification system provides a recommended therapy or treatment in real-time or near real-time. For example, a sample may be provided to the system, images may be obtained and processed, image coefficients may be extracted, a cancer cell type may be identified, and a course of action may be recommended in real-time or near real-time. One or more steps of the process may be a limiting factor, such as processing the sample for imaging and/or obtaining images. However, the system may progress rapidly once images are obtained. A report may be provided to the physician within minutes or seconds of providing a sample to the system.

Figure 2:
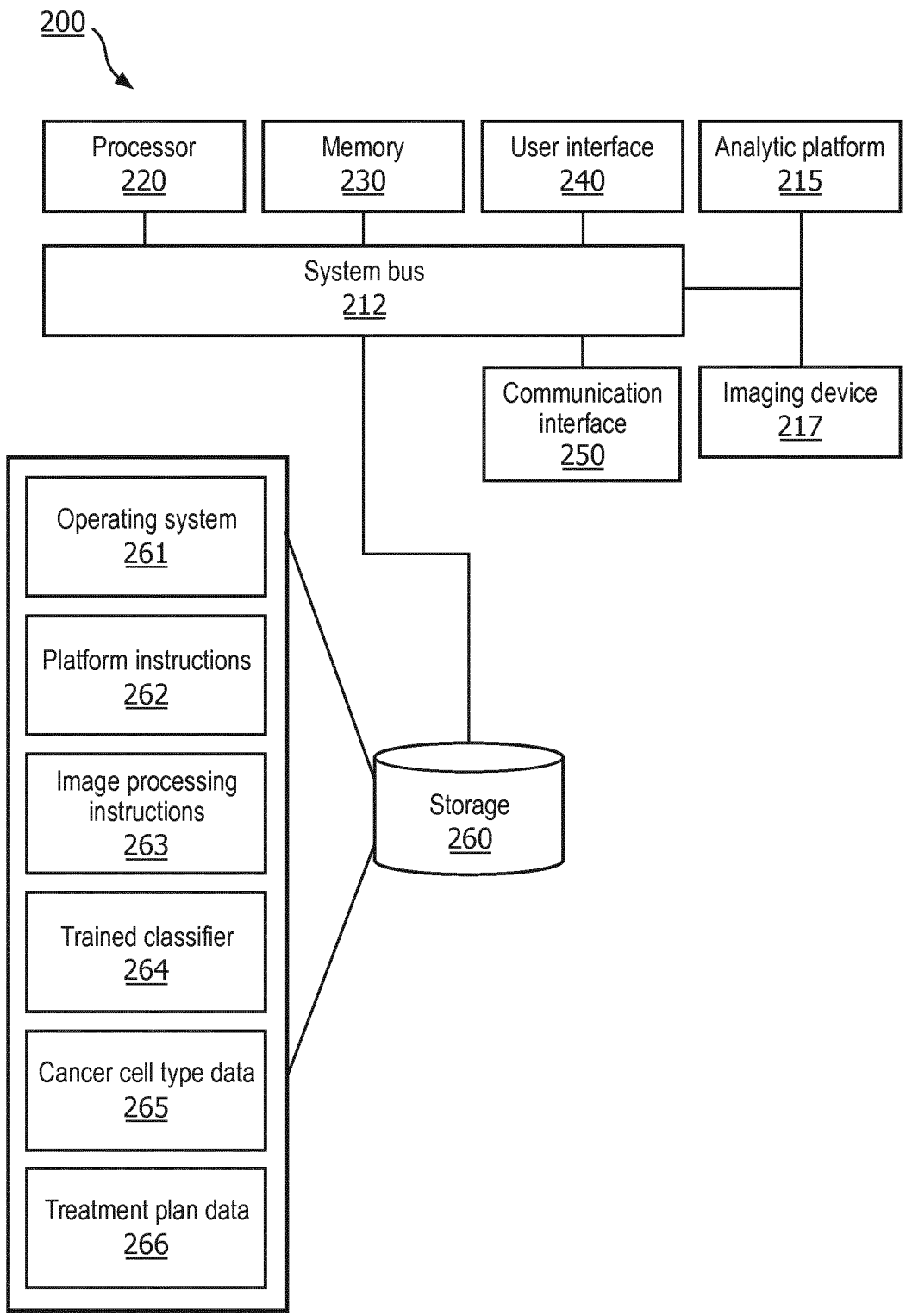
FIG. 2 is a schematic representation of a system for treating a patient diagnosed with cancer, in accordance with an embodiment.

Referring to FIG. 2, in one embodiment, is a schematic representation of a treatment identification system 200 for treating a patient diagnosed with cancer by identifying a treatment specific to the patient's cancer cell type. System 200 may be any of the systems described or otherwise envisioned herein, and may comprise any of the components described or otherwise envisioned herein.

According to an embodiment, system 200 comprises one or more of a processor 220, memory 230, user interface 240, communications interface 250, one or more imaging devices 217, and storage 260, interconnected via one or more system buses 212. In some embodiments, such as those where the system comprises or directly implements an analytic platform 215, the hardware may include additional analytic hardware such as sample processing hardware. For example, the sample processing hardware may be configured to process a fluid or tissue sample obtained from an individual, such as a biopsy sample, for imaging. It will be understood that FIG. 2 constitutes, in some respects, an abstraction and that the actual organization of the components of the system 200 may be different and more complex than illustrated.

According to an embodiment, system 200 comprises an imaging device 217 configured to obtain information about a sample from an individual. Specifically, the imaging device may be configured to obtain information about cells within the sample from the individual. The imaging device is or comprises any device or system that can obtain images or similar information from the cells in the sample. According to an embodiment, the imaging device comprises an imager configured to obtain images of one or more cells in the sample. The imager can be an image sensor such as a CCD or CMOS sensor, among others. According to another embodiment, the imaging device or imager is an audiometric signal or other audio signal that obtains information from the cells in the sample. For example, the sample can be exposed to sound waves which are used to obtain information about the cells. In one embodiment, the sound waves are converted into light by the cells and photodetectors are utilized to receive and/or process the received light into information used by the system in downstream steps of the method. Many other devices for obtaining images or similar information from a sample are possible.

According to an embodiment, system 200 comprises a processor 220 capable of executing instructions stored in memory 230 or storage 260 or otherwise processing data to, for example, perform one or more steps of the method. Processor 220 may be formed of one or multiple components. Processor 220 may take any suitable form, including but not limited to a microprocessor, microcontroller, multiple microcontrollers, circuitry, field programmable gate array (FPGA), application-specific integrated circuit (ASIC), a single processor, or plural processors.

Memory 230 can take any suitable form, including a non-volatile memory and/or RAM. The memory 230 may include various memories such as, for example L1, L2, or L3 cache or system memory. As such, the memory 230 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 200. It will be apparent that, in embodiments where the processor implements one or more of the functions described herein in hardware, the software described as corresponding to such functionality in other embodiments may be omitted.

User interface 240 may include one or more devices for enabling communication with a user. The user interface can be any device or system that allows information to be conveyed and/or received, and may include a display, a mouse, and/or a keyboard for receiving user commands. In some embodiments, user interface 240 may include a command line interface or graphical user interface that may be presented to a remote terminal via communication interface 250. The user interface may be located with one or more other components of the system, or may located remote from the system and in communication via a wired and/or wireless communications network. User interface 240 may comprise, for example, a screen for display of an identified cancer cell type or sub-type, an associated genetic signature, and/or a recommended course of action, among other information. User interface 340 may comprise, for example, a data output or retrieval mechanism for obtaining or downloading the identified cancer cell type or sub-type, associated genetic signature, and/or recommended course of action. For example, the information may be displayed on a screen, provided in a data output such as a text file or a spreadsheet, printed, or otherwise provided.

Communication interface 250 may include one or more devices for enabling communication with other hardware devices. For example, communication interface 250 may include a network interface card (NIC) configured to communicate according to the Ethernet protocol. Additionally, communication interface 250 may implement a TCP/IP stack for communication according to the TCP/IP protocols. Various alternative or additional hardware or configurations for communication interface 250 will be apparent.

Storage 260 may include one or more machine-readable storage media such as read-only memory (ROM), random-access memory (RAM), magnetic disk storage media, optical storage media, flash-memory devices, or similar storage media. In various embodiments, storage 260 may store instructions for execution by processor 220 or data upon which processor 220 may operate. For example, storage 260 may store an operating system 261 for controlling various operations of system 200. Where system 200 implements an analytic platform 215, storage 260 may include instructions 262 for operating the analytic platform 215.

It will be apparent that various information described as stored in storage 260 may be additionally or alternatively stored in memory 230. In this respect, memory 230 may also be considered to constitute a storage device and storage 260 may be considered a memory. Various other arrangements will be apparent. Further, memory 230 and storage 260 may both be considered to be non-transitory machine-readable media. As used herein, the term non-transitory will be understood to exclude transitory signals but to include all forms of storage, including both volatile and non-volatile memories.

According to an embodiment, storage 260 of system 200 may store one or more algorithms and/or instructions to carry out one or more functions or steps of the methods described or otherwise envisioned herein. For example, storage 260 may comprise image processing instructions 263. According to an embodiment, image processing instructions 263 are configured to direct the system to extract one or more image coefficients from one or more images or other data obtained or received by the system about a sample from an individual. The image processing instructions 263 may comprise or control an image processor and/or image processing algorithm in order to extract one or more image coefficients. An image coefficient may be any image coefficient that can be utilized by the treatment identification system and the trained classifier to identify the cancer cell type. For example, the image coefficient can be any quantifiable aspect of an image obtained from a cell, which can be reduced to a number. This quantifiable aspect, and the resulting number, is analyzed and quantified using one or more imagine processing techniques.

According to an embodiment, the image processing instructions 263 are configured to analyze or direct analysis of any image or information obtained from the sample, such as visual images, audiometrics from a photodetector, spectroscopy, and/or any other utilized imaging mode. The image processing algorithm can be a fractal-based image processing technique configured to process an image. The image processing algorithm can be a wavelet-based image processing technique configured to process an image. The image processing algorithm can be a spectroscopic image processing technique configured to process an image. The image processing algorithm can be a pattern-matching image processing technique configured to process an image. Many other image processing techniques are possible. Among other aspects, these image processing technique are configured to identify and quantify, as image coefficients, image features such as texture, roughness, smoothness, solidity, area, edges, heterogeneity, chemical composition, and/or other parameters of cells in the sample. The image processing technique are further configured to identify and quantify, as image coefficients, image features that are recognizable as cellular components or elements such as the contents of the cell, the nucleus, ribosomes, exosomes, vacuoles, and/or any other sub-cellular organelles or structures.

According to an embodiment, system 200 and/or storage 260 may comprise a trained classifier and/or mapping instructions 264. According to an embodiment, trained classifier and/or mapping instructions 264 are configured to direct the system to identify a cancer cell type and/or sub-type using one or more image coefficients extracted from imaging or other analysis of a sample. The trained classifier and/or mapping instructions 264 may also be configured to direct the system to identify a genetic signature associated with the one or more image coefficients and/or with the identified cancer cell type and/or sub-type. The trained classifier and/or mapping instructions 264 can be or encompass any method for the image processing and/or image coefficient mapping described or otherwise envisioned herein. The classifier and/or mapping instructions 264 may be a neural network, a decision tree, a support vector machine, a linear classifier, random forest, and/or any other type of classifier or classification algorithm. According to an embodiment, a classifier may be trained or otherwise designed or modified before installation, during installation, and/or after installation in system 200. According to an embodiment, classifier and/or mapping instructions 264 may query, consult, or interact with cancer cell type data 265.

According to an embodiment, system 200 comprises or is in communication with cancer cell type or sub-type data 265. For example, storage 360 may comprise a database 265 of cancer cell types or sub-types. Each of cancer types and sub-types are associated or correlated in the database with one or more image coefficients. Accordingly, identifying an image coefficient identifies the cancer types associated or correlated in the database with that image coefficient. Thus, the classifier and/or mapping instructions 264 can consult or query the database 265 to retrieve or otherwise identify a cancer type or sub-type using one or more image coefficients. According to an embodiment, some or all of the cancer types and sub-types are associated or correlated in the database with a genetic signature.

Accordingly, the classifier and/or mapping instructions 264 can consult or query the database 265 to retrieve or otherwise identify a cancer type or sub-type using one or more image coefficients, which also identifies one or more genetic signatures associated with that cancer type or sub-type. In some cases there may only a single possible genetic signature, while in other cases there may be two or more genetic signatures associated with the cancer type or sub-type.

According to an embodiment, system 200 comprises or is in communication with treatment plan data 266. For example, storage 360 may comprise a database 266 of cancer treatment plans. The treatment plan data comprises treatment plans, treatment recommendations, research studies, protocols, and/or other therapies associated with a cancer cell type or sub-type, and/or with a cancer-specific genetic signature. For example, a specific cancer type or the genetic signature associated with that cancer type may be associated with a chemosensitivity, radiosensitivity, or other plan, recommendation, study, research, and/or treatment recommended for that cancer type. The treatment plan data 266 may alternatively be stored in a remote public, research, medical, or paid database. Accordingly, the communication interface 250 may be in communication with the remote database via a wired and/or wireless network to retrieve one or more therapies or treatments associated with and/or recommended for treatment of an identified cancer cell type or sub-type.

Accordingly, after the image processing instructions 263 direct the system to extract the one or more image coefficients from the one or more images, and after the classifier and/or mapping instructions 264 of system 200 identifies one or more cancer cell types or sub-types, and optionally a genetic signature, using the extracted image coefficients, the system identifies one or more therapies or treatments recommended for treatment of the identified cancer cell type or sub-type, and/or the identified genetic signature. Thus, the system receives or obtains a sample or images of the sample and provides a therapy or treatment.

The identified therapy or treatment is then presented to otherwise provided to a user via user interface 240. The user interface can be any method, system, or device for conveying, displaying, or transmitting information to a user. For example, the user interface may comprise a screen, a data output or retrieval mechanism, a wired and/or wireless transceiver, or any other device. The user may be a physician or other medical professional, a researcher, the patient, or any other user. The identified therapy or treatment may be provided in any format, such as text, images, or any other format.

The methods and systems described or otherwise envisioned herein provide numerous benefits to the treatment identification system. For example, the treatment identification system provides a personalized, optimum treatment therapy for the patient. Furthermore, identification of a scientifically recommended course of treatment using an affordable diagnosis system improves quality of life and significantly reduces the cost and duration of cancer treatment.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A computer-implemented method for identifying a course of treatment specific to an identified cancer cell type in a sample from an individual, the method comprising:
    obtaining, using a CCD or CMOS imaging device, one or more images of one or more cancer cells in the sample from the individual;
    obtaining, using an audiometric imaging device, information of a second mode about the cancer cells;
    processing, using an imaging processor, both the one or more obtained images and the obtained information of a second mode about the one or more cancer cells to extract one or more image coefficients, wherein the one or more image coefficients comprises an identification of one or more image features, the image features comprising one or more cellular characteristics of the one or more cancer cells in the sample;
    mapping, using a trained classifier, the one or more image coefficients to a cancer cell type and a genetic signature associated with said cancer cell type;
    identifying, based on mapping the one or more image coefficients to a cancer cell type and associated genetic signature, one or more cancer cell types and associated genetic signatures in the sample; and
    identifying, based on the identified one or more cancer cell types and associated genetic signatures in the sample, a course of treatment specific to the one or more cancer cell types and genetic signatures.

2. The method of claim 1, wherein the cancer type is a cancer sub-type.

3. The method of claim 1, further comprising the step of reporting the identified course of treatment.

4. The method of claim 1, further comprising the step of training the classifier to map image coefficients to a cancer cell type.

5. The method of claim 1, wherein the sample is a biopsy.

6. The method of claim 1, wherein the sample is a body fluid.

7. The method of claim 1, wherein the step of processing the one or more obtained images or the obtained information of a second mode comprises fractal-based image processing, wavelet-based image processing, spectroscopic image processing, and/or pattern matching image processing.

8. A system configured to identify a course of treatment specific to an identified cancer cell type, comprising:
    a sample from an individual, the sample comprising one or more cancer cells;
    a CCD or CMOS imaging device configured to obtain one or more images of the cancer cells;
    an audiometric imaging device configured to obtain audiometric information about the cancer cells;
    a processor configured to process both the one or more images and the obtained audiometric information about the one or more cancer cells to extract one or more image coefficients, wherein the one or more image coefficients comprises an identification of one or more image features, the image features comprising one or more cellular characteristics of the one or more cancer cells in the sample; and
    a trained classifier configured to: (i) map the one or more image coefficients to a cancer cell type and associated genetic signature; and (ii) identify, based on mapping the one or more images coefficients to a cancer cell type and associated genetic signature, one or more cancer cell types and associated genetic signatures in the sample;
    wherein the processor is further configured to identify, based on the identified one or more cancer cell types and associated genetic signatures in the sample, a course of treatment specific to the one or more cancer cell types and associated genetic signatures.

9. The system of claim 8, further comprising a cancer cell type database comprising a plurality of cancer cell types each associated with one or more image coefficients, wherein the trained classifier utilizes the cancer cell type database to map the one or more image coefficients to the cancer cell type.

10. The system of claim 8, further comprising a treatment plan database comprising a plurality of treatment plans each associated with a cancer cell type, wherein the processor utilizes the treatment plan database to identify a course of treatment.

11. The system of claim 8, further comprising a user interface configured to provide a report of the identified course of treatment to a user.

12. The method of claim 1, wherein the one or more cellular characteristics of the one or more cancer cells in the sample comprises sub-cellular organelles or structures.

13. The method of claim 1, wherein the one or more cellular characteristics of the one or more cancer cells in the sample comprises a multiplication rate of the one or more cancer cells.

14. The method of claim 1, wherein the one or more image coefficients further comprises a quantification of the one or more image features.

15. The method of claim 1, further comprising:

obtaining, using a spectroscopic imaging device, information of a third mode about the cancer cells;

wherein processing, using the imaging processor, comprises processing: (1) the one or more obtained images; (2) the obtained information of a second mode; and (3) the obtained information of a third mode to extract the one or more image coefficients.

16. The system of claim 8, further comprising:

a spectroscopic imaging device configured to obtain spectroscopic information about the cancer cells;

wherein the processor is configured to process: (1) the one or more images; (2) the obtained audiometric information; and (3) the obtained spectroscopic information to extract the one or more image coefficients.

* * * * *